(12) United States Patent
Trabish

(10) Patent No.: US 8,702,805 B2
(45) Date of Patent: Apr. 22, 2014

(54) ACETABULUM SURGICAL RESURFACING AID

(76) Inventor: Harutaro Trabish, Folsom, CA (US)

( * ) Notice: Subject to any disclaimer, the term of this patent is extended or adjusted under 35 U.S.C. 154(b) by 614 days.

(21) Appl. No.: 12/497,352

(22) Filed: Jul. 2, 2009

(65) Prior Publication Data

US 2010/0016984 A1    Jan. 21, 2010

Related U.S. Application Data

(60) Provisional application No. 61/082,227, filed on Jul. 21, 2008.

(51) Int. Cl.
*A61F 2/32* (2006.01)
(52) U.S. Cl.
USPC ........................................... 623/22.12
(58) Field of Classification Search
USPC ................. 623/22.12; 606/86 R, 91, 96
See application file for complete search history.

(56) References Cited

U.S. PATENT DOCUMENTS

| | | | |
|---|---|---|---|
| 3,099,441 A | 7/1963 | Ries | |
| 3,945,377 A | 3/1976 | Kronner | |
| 4,896,663 A | 1/1990 | Vandewalls | |
| 5,766,221 A | 6/1998 | Benderev et al. | |
| 5,891,150 A | 4/1999 | Chan | |
| 5,976,149 A * | 11/1999 | Masini | 606/91 |
| 2004/0064186 A1 * | 4/2004 | McCleary et al. | 623/18.11 |
| 2004/0073225 A1 * | 4/2004 | Subba Rao | 606/91 |
| 2005/0148843 A1 * | 7/2005 | Roose | 600/407 |
| 2005/0245934 A1 | 11/2005 | Tuke et al. | |
| 2006/0058886 A1 * | 3/2006 | Wozencroft | 623/22.15 |
| 2006/0229630 A1 * | 10/2006 | Collins et al. | 606/91 |
| 2008/0287954 A1 * | 11/2008 | Kunz et al. | 606/87 |

\* cited by examiner

*Primary Examiner* — Nicholas Woodall
*Assistant Examiner* — Christine Nelson
(74) *Attorney, Agent, or Firm* — Patrick J. S. Inouye; Leonid Kisselev

(57) ABSTRACT

An acetabulum surgical resurfacing aid that includes a body conformed to fit an acetabulum of a patient is presented. A portion of the body is further conformed to fit an acetabular fossa of the patient. One or more arms extend outward from the body and are configured to fit the surface of the acetabulum. A support extends from the body beyond the acetabulum. An alignment tube guide connects to the support.

12 Claims, 3 Drawing Sheets

40

ACETABULUM SURGICAL RESURFACING AID

CROSS-REFERENCE

This non-provisional patent application claims priority under 35 USC §119(e) to U.S. provisional patent application, entitled "Custom Self Clamping Hip Resurfacing Surgical Aid," Ser. No. 61/082,227, filed Jul. 21, 2008, the disclosure of which is incorporated by reference.

FIELD

The present invention relates in general to hip resurfacing surgical aids and, in particular, to an acetabulum surgical resurfacing aid.

BACKGROUND

Joint cartilage is fibrous connective tissue providing cushioning between bones. Disease and physical disorders, such as osteoarthritis, rheumatoid arthritis, and avascular necrosis; benign or malignant bone tumors; excessive physical activity; and hereditary defects can cause cartilage tearing, erosion, or degeneration. Osteoarthritis, for instance, can occur following trauma to a joint region, or due to genetic predisposition or obesity. The disease is characterized by a premature wearing down or "erosion" of the cartilage surrounding a joint between two bones. The wear can lead to the bones rubbing directly against one another, which in turn causes pitting and malformation of the bone surfaces accompanied by pain and encumbrance of range of motion. Osteoarthritis treatment regimens include resting the affected joint, prescription of pain relief and anti-inflammatory medication, improved diet, and low impact exercise. In severe cases, surgical intervention, such as arthroplasty surgical procedures, may be necessary to repair the damaged or dysfunctional joint surfaces.

Hip joints are particularly susceptible to cartilage compromise and hip arthroplasty, commonly called "total hip replacement" (THR), attempts to relieve the pain associated with, and to restore the integrity and functionality of, damaged hip joints. In THR, the upper portion of the femur, including the femoral head and neck, is removed to receive the stem portion of a prosthetic implant. While generally successful, further post-THR hip joint deterioration may necessitate revision surgery, which entails radical femur restructuring by splitting apart the femur to remove the THR prosthesis stem and surgically rebuilding the femur, a more costly and involved procedure with extended convalescence.

Recently, hip resurfacing has emerged as a viable surgical alternative to THR, which is especially suitable for younger and more active patients. Hip resurfacing entails implantation of a hip joint prosthesis, generally formed of a femoral head prosthesis and an acetabular prosthesis. Unlike THR, the upper portion of the femur is retained intact and the femoral head is, instead reshaped to accept a less extensive prosthetic femoral cap. Resurfacing requires less bone removal, which can result in easier revision surgery, if later needed, by preserving more bone stock.

Precise alignment of the femoral head prosthesis along the central access of the femoral neck and of the acetabular prosthesis to the acetabulum is essential to successful hip resurfacing. Any misalignment can result in pain and affect the degree of leg extension and joint rotation. Typically, X-rays, computed tomography (CT) scans, magnetic resonance imaging (MRI), or other forms of non-invasive imaging are taken of the hip joint and surrounding bony structures for planning the hip resurfacing procedure. Surgical templates are used along with the images to approximate the size and implantation axis of the prosthesis.

The preoperatively planned positions of the femoral head prosthesis and acetabular prosthesis must be transferred to the actual patient in the surgical theater, which is a manual and inherently imprecise process. During conventional hip resurfacing surgery, the acetabulum is resurfaced along a preoperatively planned acetabular prosthesis implantation axis. Determining the position and axis of the acetabular prostheses during surgery, even with preoperative planning, is a manual, lengthy, and potentially error prone procedure, highly dependent upon the skill of the surgeon, quality of imaging, and patient condition.

Conventionally, the implantation axis of the acetabular prosthesis is manually approximated using a reaming device prior to proceeding with the acetabular resurfacing surgery. Alternatively, a guide wire can be inserted into a nearby bone region of the patient along the approximated implantation axis. With practice, an acceptable guide wire position can be determined, yet correct placement requires frequent manual readjustments of the guide wire before proceeding with reaming of the acetabulum.

SUMMARY

An embodiment provides an acetabulum surgical resurfacing aid that includes a body conformed to fit an acetabulum of a patient. A portion of the body is further conformed to fit an acetabular fossa of the patient. One or more arms extend outward from the body and are configured to fit the surface of the acetabulum. A support extends from the body beyond the acetabulum. An alignment tube guide connects to the support.

A further embodiment provides a method for aligning an acetabulum prosthesis axis. And acetabulum surgical resurfacing aid is provided and includes a body conformed to fit an acetabulum of a patient. A portion of the body is further conformed to fit an acetabular fossa of the patient. One or more arms extend outward from the body and are configured to fit the surface of the acetabulum. A tube guide extends from the body beyond the acetabulum. The tube guide defines an axis parallel to a planned acetabular prosthesis axis. The acetabulum surgical resurfacing aid is placed in position in the acetabulum of the patient. A guide rod is inserted through the tube guide and into a pelvis of the patient.

Still other embodiments will become readily apparent to those skilled in the art from the following detailed description, wherein are described embodiments by way of illustrating the best mode contemplated. As will be realized, other and different embodiments are possible and their several details are capable of modifications in various obvious respects, all without departing from the spirit and the scope. Accordingly, the drawings and detailed description are to be regarded as illustrative in nature and not as restrictive.

DETAILED DESCRIPTION

Figure 1:
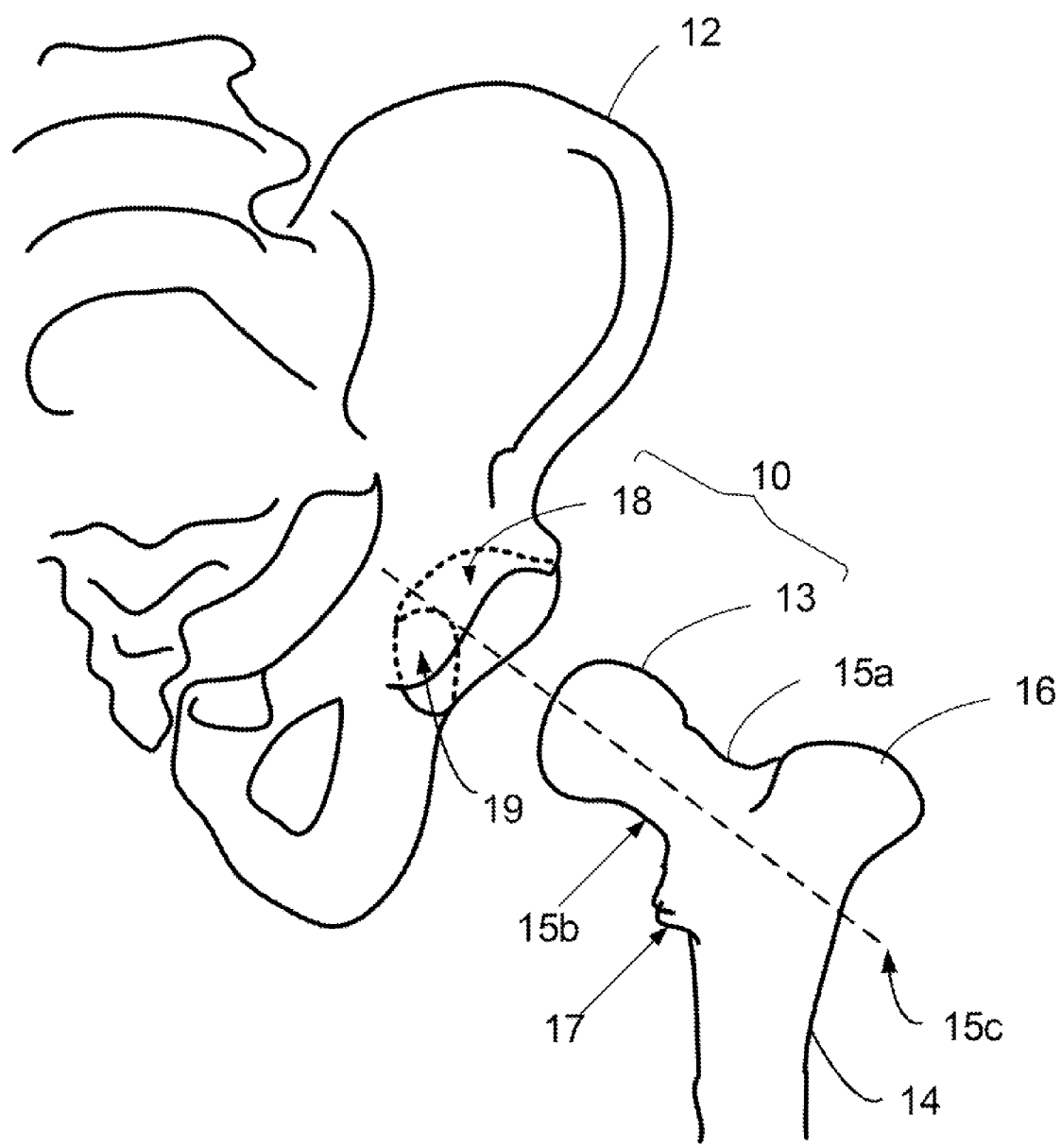
FIG. 1 is a side view showing, by way of example, a hip joint with the femur dislocated from the pelvis for clarity.

The hip joint is key to providing both mobility during walking and running and to ensuring stability during standing and other weight-bearing activities. The hip joint provides an important shock absorption function to the upper body due to impact from walking. As way of background, FIG. 1 is a side view showing, by way of example, a hip joint 10 with the femur 11 dislocated from the pelvis 12 for clarity. A femoral head 13 forms a ball at the proximal end of the femoral body 14 separated by a femoral neck 15a that meets the femoral head 13 at the femoral head-neck junction 15b. Greater trochanter 16 and lesser trochanter 17 bony prominences abutting the femoral body 14 form a base from which the femoral neck 15a extends. In a healthy patient, cartilage covers the femoral head 13 and provides cushioning between the femoral head 13 and pelvis 12.

The femoral head 13 articulates within the pelvis 12 at the acetabulum 18 to form the hip joint 10. The acetabulum 18 forms a cup-shaped depression on either side of the pelvis 12 to receive the femoral head 13. The acetabular fossa 19 is an indented region located at the bottom of the cavity of the acetabulum 17. Implantation of a femoral head prosthesis, as further described infra, and alignment of a reaming device for resurfacing of the femoral head 13 in preparation for the prosthesis, is ideally along the central axis 15c of the femoral neck 15a.

Figure 2:
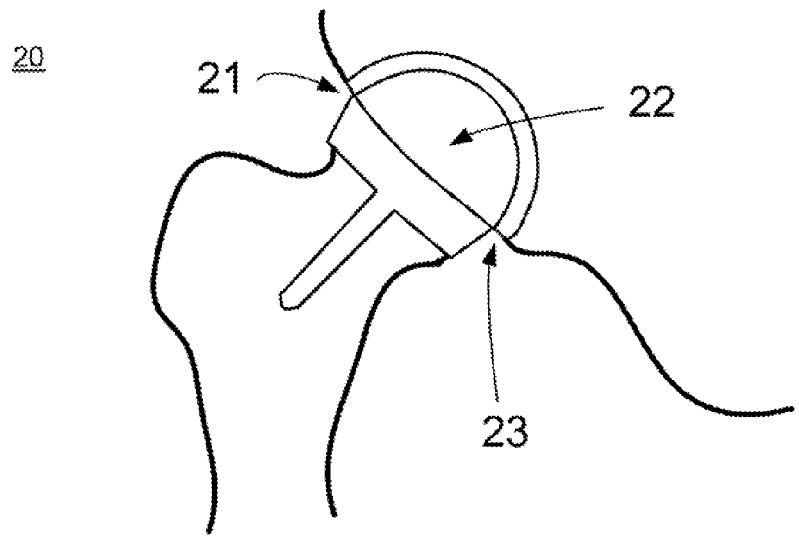
FIG. 2 is a side view showing a prior art resurfaced hip joint.

During hip resurfacing surgery, hip joint cartilage is removed and a hip joint prosthesis 21 implanted to replace the natural hip joint 10. FIG. 2 is a side view showing a prior art resurfaced hip joint 20. A full hip joint prosthesis 21 has two parts: a femoral head prosthesis 22 and an acetabular prosthesis 23, which respectively replace the functionality of the femoral head 13 and acetabulum 17. The femoral head prosthesis 22 is implanted into the resurfaced femoral head 13, while the acetabular prosthesis 23 is implanted in the acetabulum 17.

Conventionally, surgeons rely on non-invasive imaging, for example, X-ray, CT scan, and MRI, to determine the approximate sizes and alignments of the amoral head prosthesis 22 and acetabular prosthesis 23. In surgery, the femoral head 13 is dislocated and the approximated size of the femoral head prosthesis 23 is confirmed in situ by placing a surgical head template around the femoral neck 15a.

Accurate determination of the position on the femoral head 13 relative to the central axis of the femoral neck 15a is critical to the correct positioning of the guide wire, the various cutters, reamers, and reshaper tools, and the femoral head prosthesis 22 during surgery. Moreover, insufficient clearance for the femoral head prosthesis 22 can lead to notching of the femoral neck 15a during resurfacing by the reaming device and weakening of the post-surgical hip. A jig (not shown) is utilized to determine the point on the femoral head 13 that aligns with the central axis 15c of the femoral neck 15a. The jig is generally attached to or placed circumferentially on the femur 11. A guide mechanism on the jig can be adjusted through all dimensional planes to confirm the correct axis of alignment for the femoral head prosthesis 22. Once aligned, the guide mechanism can be locked into position on the jig and a guide wire is inserted into the femoral head 13 along the determined axis, after which the jig is disassembled and removed. A reaming device mounts to the guide wire and trims the femoral head 13 flush to the femoral neck 15a. The femoral head 13 can be trimmed further, as necessary, so that the mouth of the femoral head prosthesis 22 is at the level of the femoral head-neck junction 15b. Another reaming device cuts a chamfer, or beveled edge, on the femoral head 13. The guide wire is removed and the femoral head prosthesis 22 cemented into place.

Similarly, correct determination of the axis of placement of the acetabulum reaming device is necessary for correct placement of the acetabular prosthesis 23. Conventionally, the axis is manually approximated by the surgeon either during the reaming process or by positioning a guide near the acetabulum 18 at an angle approximating the planned axis. The acectabulum 18 is prepared for the acetabular prosthesis 23 by first removing cartilage and any osteophytes that may have formed. The acetabulum is then reduced to receive the acetabular prosthesis 23. The pre-operative axis of the acetabular prosthesis 23 is adjusted, as necessary, and impacted into position.

Figure 3:
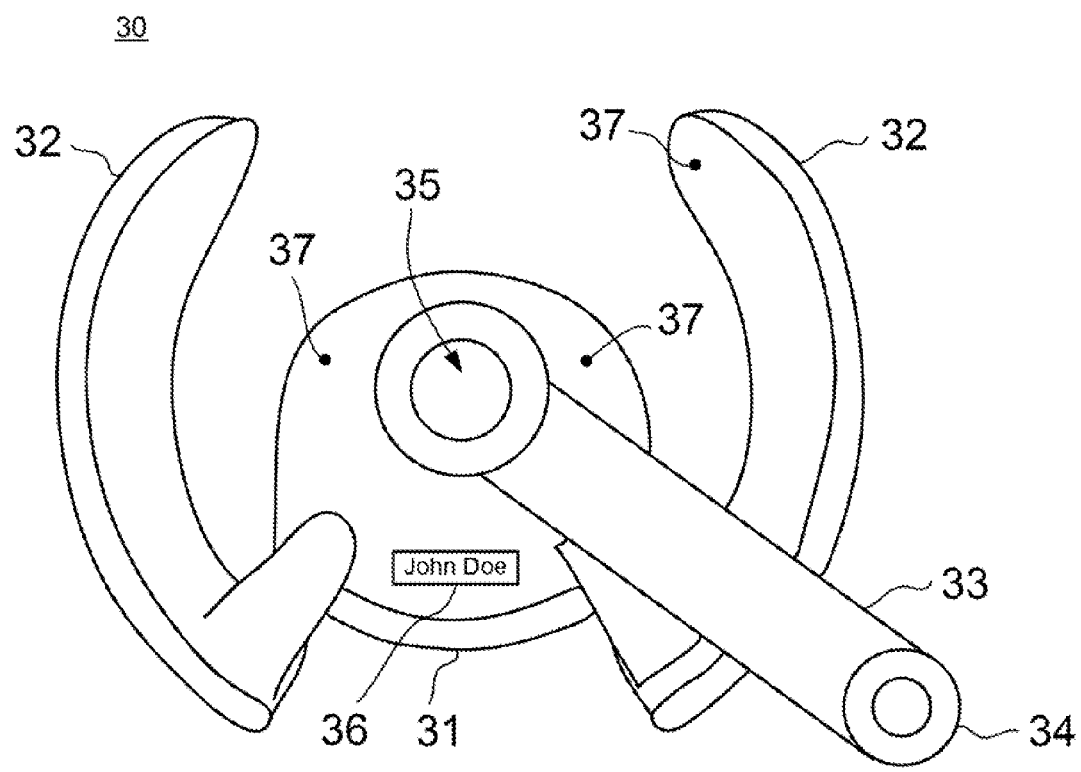
FIG. 3 is a perspective view showing an acectabulum surgical resurfacing aid in accordance with one embodiment.

Rapid and precise placement of the acetabular prosthesis 23 along a pre-operatively planned implantation axis can be facilitated by replacing prior art hip resurfacing surgical alignment guides with acetabulum surgical resurfacing aids that are custom-designed to patient specific features. FIG. 3 is a perspective view showing an acectabulum surgical resurfacing aid 30 in accordance with one embodiment. The acectabulum surgical resurfacing aid 30 enables efficient and fixed placement and ready removal of the aid 30. Each aid 30 is uniformly fabricated from a biocompatible, flexible material. Preferably, the material is well suited for rapid prototype manufacturing, as further described infra. Examples of such material include medical grade plastics, such as polycarbonate or acrylonitrile butadiene styrene (ABS). Other materials for construction of the acectabulum surgical resurfacing aid 30 are possible.

The acectabulum surgical resurfacing aid 30 includes a body 31 that is curved to fit snugly and conformably inside the acetabulum 18, which inhibits movement or slippage. Additionally, a portion of the body 31 is further conformed to fit into the acetabular fossa 19. Two or more arms 32 extend from the body 31 and are, likewise, conformed to match the inside surface of the acetabulum 18. The acectabulum surgical resurfacing aid 30 is placed in situ by providing inward pressure on the arms 32 towards one another and inserting the body 31 into the acetabulum 18 and acetabular fossa 19. The flexible material used for the construction of the aid 30 provides tension and purchase for the arms to press against the surface of the acetabulum 18 to maintain aid 30 position in situ. Placing the acetabulum surgical resurfacing aid 30 into the acetabulum fossa 19 provides proper alignment of the aid 30 without the need for further adjustment.

A support 33 extends outward from the body 31 beyond the acetabulum 18 and connects to an alignment tube guide 34. The support 33 extends out of the acetabulum 18 such that the axis of the alignment tube guide 34 is parallel to the axis of a pre-operatively planned acetabulum prosthesis 22 axis. The interior diameter of the alignment tube guide 34 is sized to receive a guide rod (not shown), which is inserted through the alignment tube guide 34 and into the pelvis, as discussed further below with reference to FIG. 4. In one embodiment the support 33 is 45 millimeters in length, while the interior diameter of the alignment tube guide 34 is four millimeters. Other dimensions are possible. The support 33 and alignment tube guide 34 are integrally constructed as part of the acetabulum surgical resurfacing aid 30, as further described infra.

In a further embodiment, a segment 35 of the body 31 is configured to receive a device, such as tool or finger, to provide further support to the acectabulum surgical resurfacing aid 30 from moving in situ during insertion of the guide rod. The segment 35 can be slightly recessed or protruding from the body 31. Once the guide rod is positioned, the acetabulum surgical resurfacing aid 30 is removed, as further discussed below with reference to FIG. 4. Acetabulum resurfacing then proceeds as discussed above with reference to FIG. 2.

Preferably, the acectabulum surgical resurfacing aid 30 is rapid prototyped based on patient-specific physical femoral features. A patient's hip joint region is scanned using a non-invasive imaging technique, such as CT or MRI. The imaging is imported into a computer aided design (CAD) program or other three-dimensional modeling software loaded into a computer system, for example, 3D-DOCTOR, available from Able Software Corporation, Lexington, Mass. The computer system is a general purpose, programmed digital computing device consisting of a central processing unit (CPU), random access memory (RAM), non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage.

The CAD program segments the bone structures to create a three-dimensional model of the acetabulum 18 and the femur 11. The three-dimensional model is then used for preoperative planning of the size and implantation axis of the acetabular prosthesis 23 according to the anatomical structure of the patient. Additionally, key landmark points within the acetabulum 18 are identified, including bony structures and protuberances, and depressions, ridges, scars, and striations.

A three-dimensional model of the acetabulum surgical resurfacing aid 30 is generated by the CAD program using the key landmark points, the patient-specific surface structure of the acetabulum 18, and the planned position of the acetabular prosthesis 23. For example the surface structure and key landmarks of the acetabulum 18 are used to render the dimensions, shape, and outside surface of the body 31 and arms 32 to conformably follow the acetabulum 18 contours. Similarly, the planned axis of the acetabulum prosthesis 23 is used to position the support 33 and alignment tube guide 34. The model of the acetabulum surgical resurfacing aid 30 is stored in memory and is provided to or electronically transmitted over an intranetwork or internetwork, such as the Internet, to a rapid prototype system, such as the FDM 400mc, manufactured by Stratasys, Inc., Eden Prairie, Minn., to fabricate the aid 30.

In a further embodiment, an existing acetabulum surgical resurfacing aid 30 model is digitally manipulated by morphing, stretching, and warping to create the patient-specific model based on the anatomical structures of the patient, the key landmark points, and the planned prosthesis position. The model can be viewed and adjusted as necessary prior to fabrication.

In a still further embodiment, patient information 36 can be printed, engraved or marked on the surface of the aid 30. Patient information can include patient name, patient identification number, name of surgeon, hospital name, identification of which hip joint is to be replaced, and the type and size of prosthesis to be used. Including patient information 36 directly on the aid 30 can assist with routing the aid 30 to the proper patient or hospital and aid the surgeon while performing surgery, such as circumstances wherein a patient is undergoing total hip replacement on both hips simultaneously.

Figure 4:
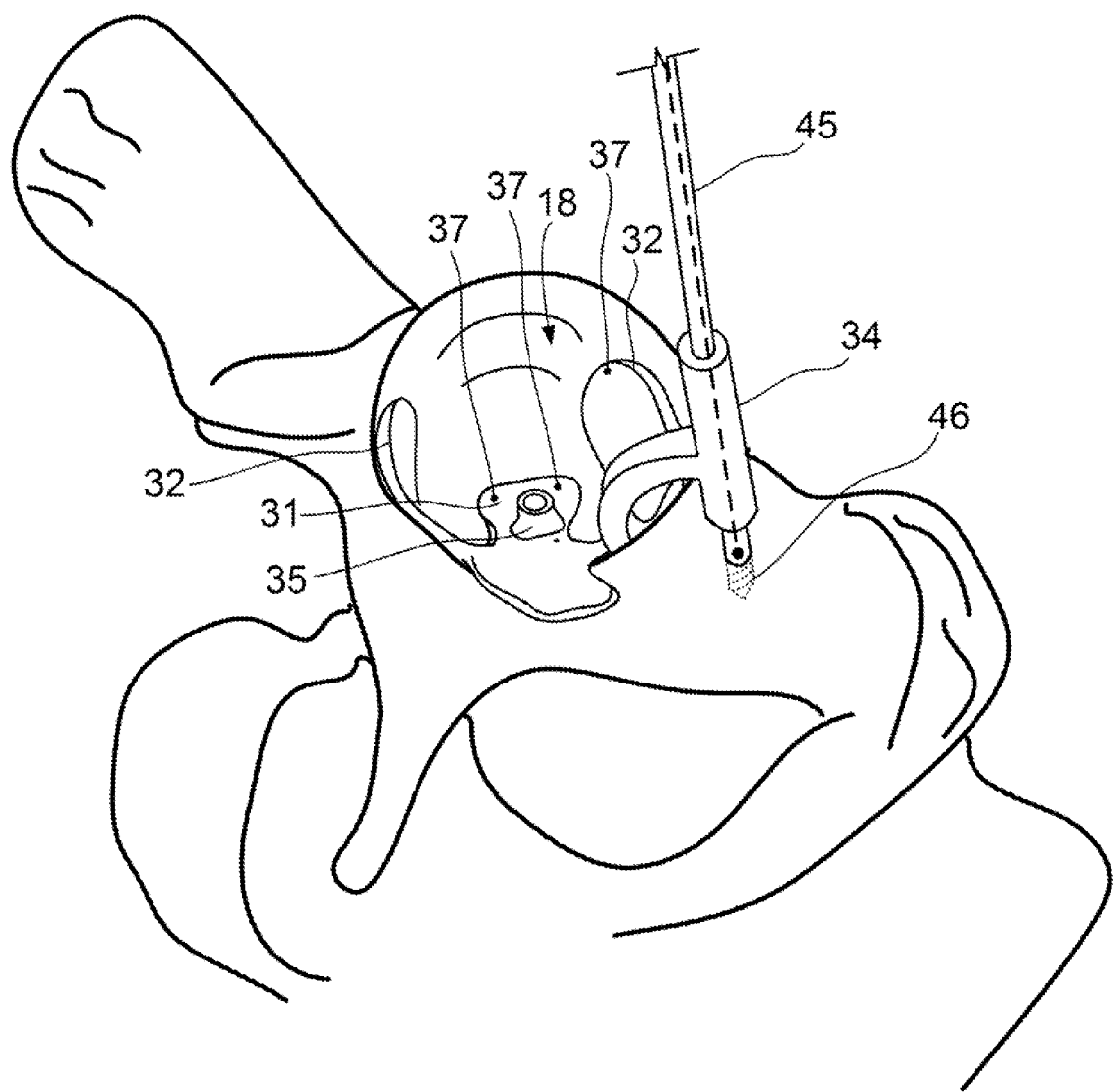
FIG. 4 is a perspective view showing the acectabulum surgical resurfacing aid in position in the acetabulum.

The acetabulum surgical resurfacing aid 30 is used to accurately align the acetabulum prosthesis 23 according to a pre-operative plan. FIG. 4 is a perspective view showing the acetabulum surgical resurfacing aid 30 in position in the acetabulum 18. The acetabulum surgical resurfacing aid 30 is placed into position by applying inward pressure on the arms 32 toward one another, inserting the aid 30 into the acetabulum 18, and then releasing the arms 32. The body 31 conformably follows the surface of the acetabulum 18 and acetabular fossa 19 when placed into position in situ. Matching the surface of the acetabulum 18 allows the aid 30 to fit in only one orientation. Additionally, the arms 32, when released, conformably follow the surface of the acetabulum 18. Once inserted, the arms 32 remain slightly compressed providing additional purchase during surgical manipulation.

The support 33 extends outward from the body 31 of the acetabulum prosthesis aid 30 and protrudes out of the acetabulum 18. The support 33 connects to the alignment tube guide 34 at a point outside the perimeter of the acetabulum 18. The axis of the alignment tube guide 34 is parallel to the pre-planned axis of the acetabulum prosthesis 23 in situ. Once the aid 30 is in position in the acetabulum 18, a guide rod 45 is inserted through the alignment tube guide 34 and into the pelvis 12. In a further embodiment, the guide rod 45 includes a self-screwing end, which is used to place the guide rod into the pelvis 12. Preferably, the guide rod 45 is inserted into the pelvis 12 at a point 36 in the central region of the ischium bone inferior to the spine of the ischium. Other insertion points are possible. Once inserted into the pelvis 12, the axis of the guide rod 45 is parallel to the pre-operatively planned axis of the acetabulum prosthesis 23. The guide rod 45 is then used as a reference for the angle of the reaming device and subsequent placement of the acetabulum prosthesis 23.

In a further embodiment, a segment 35 of the body 31 is configured to receive a device, such as tool or finger, to provide further support to, and prevent movement of, the acetabulum alignment aid 30 during placement of the guide rod 45. The segment 35 can be slightly recessed or protruding from the body 31. Other segment configurations are possible.

The acetabulum surgical resurfacing aid 30 is then efficiently removed by providing inward pressure on the arms 32 toward one another and sliding the alignment tube guide 34 over the guide rod 45. The guide rod 35 is then used as a visible guide to align the reaming device and acetabulum resurfacing surgery proceeds as discussed above with reference to FIG. 2. After the acetabulum 18 is properly reamed, the guide rod 35 is removed from the pelvis 12.

In a further embodiment, the acetabulum surgical resurfacing aid 30 contains one or more fixed points 37 that can provide further confirmation the aid 30 is properly placed. Conventionally, a digitizer coupled to a navigation system is used to register, or map, points on the surface of bone to their corresponding position in a scanned image of the bone. Such feature-based registration can aid in correct positioning of implants during computer-assisted surgery. Similarly, the fixed points 37 of the acetabulum surgical resurfacing aid 30 can be used to register the position of the fixed points with positions in a scanned image of bone structures, such as discussed supra. The registration can then provide additional verification that the aid 30 is in the correct position in the acetabulum 18. The fixed points 37 can be added to the acetabulum surgical resurfacing aid 30 as part of the three-dimensional model generation process, as discussed supra. In a further embodiment, the fixed points 37 can be added post-fabrication. The fixed points 37 can be depressions or holes in, or protrusions from, the outer surface of the aid 30. Other types of fixed points are possible.

While the invention has been particularly shown and described as referenced to the embodiments thereof, those skilled in the art will understand that the foregoing and other changes in form and detail may be made therein without departing from the spirit and scope of the invention.

What is claimed is:

1. An acetabulum surgical resurfacing aid, comprising:
   a body conformed to fit against an inside surface of an acetabulum of a patient;

a portion of the body conformed to fit into the acetabular fossa of the acetabulum;

two or more arms extending outward from the body and conformed to compress in response to pressure and to press against the inside surface of the acetabulum when in position and the pressure is released, wherein the arms pressing against the inside surface of the acetabulum maintain the body in place within the acetabulum;

a support extending outward from the body beyond the acetabulum; and an alignment tube guide connected to the support, wherein the alignment tube guide defines an axis parallel to a planned acetabular prosthesis axis.

2. An acetabulum surgical resurfacing aid according to claim 1, wherein the alignment tube guide is configured to receive a guide rod.

3. An acetabulum surgical resurfacing aid according to claim 1, wherein the guide rod comprises a self-screwing end.

4. An acetabulum surgical resurfacing aid according to claim 1, wherein the aid is composed of a biocompatible, flexible, medical grade material.

5. An acetabulum surgical resurfacing aid according to claim 1, wherein the material is selected from one of polycarbonate and acrylonitrile butadiene styrene.

6. An acetabulum surgical resurfacing aid according to claim 1, the body is further configured to receive a tool.

7. An acetabulum surgical resurfacing aid according to claim 1, wherein the aid is inscribed with at least one of a patient information and prosthesis information.

8. An acetabulum surgical resurfacing aid according to claim 1, wherein the body further comprises one or more fixed registration points on an outer surface of the body that are used to register positions in a scanned image of bony structures of the acetabulum.

9. An acetabulum surgical resurfacing aid according to claim 1, wherein the support extends from the body at a position inward from the edge of the body.

10. An acetabulum surgical resurfacing aid according to claim 1, wherein the two arms extend from the body in mirror image arcs of one another.

11. An acetabulum surgical resurfacing aid according to claim 1, wherein the aid is uniformly fabricated and the support and the alignment tube guide are integrally constructed as a part of the aid.

12. An acetabulum surgical resurfacing aid according to claim 1, wherein the surface of the body is conformed to fit against any bony structures, protuberances, depressions, ridges, scars, and striations of the acetabulum.

* * * * *